United States Patent

Reichenberger et al.

Patent Number: 5,370,121
Date of Patent: Dec. 6, 1994

[54] METHOD AND APPARATUS FOR NON-INVASIVE MEASUREMENT OF A TEMPERATURE CHANGE IN A SUBJECT

[75] Inventors: Helmut Reichenberger, Eckental; Guenter Temme, Spardorf, both of Germany

[73] Assignee: Siemens Aktiengesellschaft, Munich, Germany

[21] Appl. No.: 115,557

[22] Filed: Sep. 3, 1993

[30] Foreign Application Priority Data

Sep. 7, 1992 [DE] Germany .................. 4229817

[51] Int. Cl.$^5$ ................................. A61B 8/00
[52] U.S. Cl. ................... 128/660.02; 128/660.03; 128/736; 374/117
[58] Field of Search .............. 128/660.01, 660.02, 128/660.03, 736; 607/97, 102; 73/117

[56] References Cited

U.S. PATENT DOCUMENTS

| | | | |
|---|---|---|---|
| 3,735,755 | 5/1973 | Eggleton et al. | 128/24 |
| 4,265,121 | 5/1981 | Cribbs | 73/607 |
| 4,513,749 | 4/1985 | Kino et al. | 128/660.02 |
| 4,566,459 | 1/1986 | Umemura et al. | 128/660 |
| 4,566,460 | 1/1986 | Sato et al. | 128/660 |
| 4,754,760 | 7/1988 | Fukukita et al. | 128/660.02 |
| 4,807,633 | 2/1989 | Fry | 128/660.02 |
| 4,817,615 | 4/1989 | Fukukita et al. | 128/660.02 |
| 5,143,073 | 9/1992 | Dory | 128/660.03 |
| 5,150,712 | 9/1992 | Dory | 128/660.03 |

FOREIGN PATENT DOCUMENTS

| | | | |
|---|---|---|---|
| 1698107 | 8/1971 | Germany | G01N 29/00 |
| 3137581 | 10/1983 | Germany | G01K 11/22 |
| 3616214 | 12/1987 | Germany | G03B 42/06 |

OTHER PUBLICATIONS

Patents Abstracts of Japan, P-574, May 12, 1987, vol. 11/No. 144, Application No. 60-122139.
Patents Abstracts of Japan, P-1251, Sep. 12, 1991, vol. 15/No. 363, Application No. 64-279091.
"Ultraschall," Herfroth et al, pp. 140-143.
"A Therapeutic Ultrasound System Incorporating Real-Time Ultrasonic Scanning," Lizzi et al, 1986 Ultrasonics Symposium, pp. 981-984.
"High Intensity Focused Ultrasound-A Surgical Technique For The Treatment of Discrete Liver Tumors," ter Haar et al, Phys. Med. Biol., 1989, vol. 34, No. 11, pp. 1743-1750.
"Focussed Extracorporeal Pyrotherapy: Experimental Results," Vallancien et al, Eur. Urol. 1991, vol. 20, pp. 211-219.
"Ultrasonic Speed As A Parameter For Non-Invasive Thermometry," Nasoni et al (1987).
D. Husson et al "Remote Temperature Measurement Using an Acoustic Probe", 320 Applied Physics Letters vol. 41 (1982) Nov. No. 10, New York, USA.

*Primary Examiner*—Francis Jaworski
*Attorney, Agent, or Firm*—Hill, Steadman & Simpson

[57] ABSTRACT

A method and apparatus for non-destructively or non-invasively measuring a temperature change in the inside of a subject, in particular a living subject, identify the temperature change in a region of interest during the course of producing ultrasound images of the region by determining the change of the acoustic impedance of the region of interest, and allocating a temperature change to the impedance change. An installation for treating a living subject with heating radiation which employs the above method and apparatus for measuring the temperature change of a region of treatment, is also disclosed.

24 Claims, 2 Drawing Sheets

METHOD AND APPARATUS FOR NON-INVASIVE MEASUREMENT OF A TEMPERATURE CHANGE IN A SUBJECT

BACKGROUND OF THE INVENTION

1. Field Of the Invention

The present invention is directed to a method for non-destructive or non-invasive measurement of a temperature change occurring in the inside of a subject, in particular, a living subject, between two successive points in time, and to an apparatus for the implementation of the method, as well as to an installation making use of the method and the apparatus for treating a living subject with radiation that heats at least an internal region of the body of the subject.

2. Description of the Prior Art

In a large variety of circumstances, there is a need for technology to be able to measure temperature changes, particularly the temperature elevation resulting from heating, in the inside of a subject in a non-destructive way, i.e., without a temperature-measuring probe matched to the respective requirements being attached in the region to be examined. This is partly because it is usually necessary to modify the subject to be examined in order to bring the probe into proximity with the internal region whose temperature is to be measured, for example to provide bores or the like for the temperature-measuring probe. A comparable problem also arises in medicine, since it is often desirable to be able to measure the temperature existing in the inside of the body of a living subject, namely a patient, without invasive measures such as the introduction of a temperature-measuring probe, being necessary. Such a method would be of special interest in combination with the therapeutic application of heating radiation (hyperthermia), for example microwaves or focused, high-intensity ultrasound, wherein tumor tissue or other pathological tissue zones are intentionally heated in order to cause necrosis of the heated tissue, and in combination with an apparatus for the implementation of such therapies.

SUMMARY OF THE INVENTION

It is therefore an object of the present invention to provide a method for non-destructive or non-invasive measurement of a temperature change in the inside of a subject, in particular, a living subject.

It is a further object to provide an apparatus for the implementation of such a method.

It is a further object to provide an installation that makes use of the method and the apparatus for treating a life form.

A method in accordance with the invention for non-destructive or non-invasive measurement of a temperature change in the inside of a subject, such as a living subject, that occurs between two successive points in time includes the following method steps. An acoustic waveform containing at least one acoustic pulse is radiated into the subject at a first point in time such that it radiates a region to be examined. The echo signals which arise due to reflection of the waveform at the region to be examined are received and stored. A waveform that is identical to the waveform radiated at the first point in time is radiated into the subject in an identical way at a second point in time. The echo signals which arise by reflection of the waveform radiated at the second point in time at the region to be examined are received. The echo signals belonging to the first and to the second points in time are compared to one another, preferably by the formation of a difference. A temperature change of the region to be examined is determined from the result of the comparison.

The invention utilizes the fact that practically all substances have an acoustic impedance that varies dependent on the temperature. The acoustic impedance corresponds to the product of the density of the substance and the speed of sound therein. For a human tissue, for the temperature range from approximately 35° through 50° C. that is of special interest, for example, the speed of sound increases by approximately 0.08%/°C. and the density decreases by approximately 0.04%/°C. This results in a change of the acoustic impedance of 0.04%/°C. It is thus possible to determine corresponding, temperature-related data from the acoustic impedance of the region to be examined. As used herein, the term "data" does not limit the temperature-related data as being only in the form of digital data; analog signals can also be used. On the basis of the temperature-related data belonging to the successive points in time, the temperature change that occurred in the region to be examined between the points in time can then be determined, for instance by calculation, or the occurrence of a temperature change, particularly a temperature elevation, can be identified.

Methods for non-destructive or non-invasive measurement of the acoustic impedance present in the inside of a subject are known from non-destructive materials testing and from medical ultrasound imaging. It is consequently provided in a version of the invention that the irradiation by the waveforms and the reception of the corresponding echo signals respectively ensue such that an ultrasound image of the region to be examined is produced, and that differential images of the ultrasound images belonging to the points in time are formed for measuring the temperature change occurring between the first and the second point in time, the temperature change for the region to be examined being determined from these ultrasound images. This offers the advantage that an unambiguous identification of the region to be examined is possible in the ultrasound image, so that a high topical resolution of the measurement can be achieved. Moreover, the formation of the difference need not be carried out for the ultrasound images in toto. On the contrary, it is adequate to form this difference only for the region to be examined known as the region of interest, or ROI. An ultrasound tomogram, for example, an ultrasound B-image, is preferably produced as the ultrasound image in this version of the invention.

The localization of a temperature change of a region to be heated in the inside of a subject, in particular a living subject, that occurs between two successive points in time inventively ensues with the following methods steps. At a first point in time, an acoustic waveform containing at least one acoustic pulse is radiated into the subject such that it radiates the region to be examined, which at least partially contains the region to be heated. The echo signals that arise due to reflection of the waveform at the region to be examined are received and stored. At a second point in time, a waveform that is identical to the waveform radiated at the first point in time is radiated into the subject in an identical way. The echo signals that arise due to reflection of the waveform radiated at the second point in time at the region to be examined are received. The echo signals belonging to the first and to the second points in time are compared to one another, preferably by the formation of differences. A determination is made on the basis of the result of the comparison whether a temperature change of the region to be examined has occurred and, if it has, whether this has occurred within that part of the region to be heated that lies within the region to be examined.

It is thus possible to determine whether a temperature elevating in fact ensued within the intended region. This is particularly critical in medical applications, since heating outside of the intended region to be heated can lead to damage to healthy tissue. The radiation and the reception of the waveform in a version of the invention can again ensue in such a way that ultrasound images belonging to the first and second points in time are produced and a differential image is formed. The location of a potential temperature change is determined therefrom.

An apparatus for the implementation of the method inventively includes the following: an ultrasound imaging system having a display for the presentation of ultrasound images, an image memory for an ultrasound image generated with the ultrasound imaging system, a subtractor that subtracts the stored ultrasound image from a chronologically following ultrasound image, and an evaluation unit which identifies the temperature change that occurred between the points in time of the ultrasound imaging with reference to the differential image.

The identification of temperature changes that occurred between successive points in time is possible with high precision by producing ultrasound images at the identified points in time. In certain instances, for example when the time required for the formation of the differential image is longer than the time required for generating an ultrasound image and a continuous observation of the region to be examined is desirable with the ultrasound imaging means, it can be expedient to provide a further image memory for the chronologically following ultrasound image.

When, in a preferred version of the invention, the ultrasound imaging generates tomograms, particularly ultrasound B-images, a commercially available diagnostic ultrasound apparatus can be advantageously employed as the ultrasound imaging system, which is modified to include the evaluation unit, possibly an image memory (or memories), as well as a subtractor.

An apparatus constructed in accordance with the invention, with which the localization of a temperature change of a region to be heated that occurred between two successive points in time is possible in the inside of a subject, in particular, a living subject includes the following: an ultrasound imaging system having a display for the presentation of ultrasound images, an image memory for an ultrasound image generated with the ultrasound imaging system, a subtractor that subtracts the stored ultrasound image from a chronologically following ultrasound image, and an evaluation unit which identifies the location of a temperature change (if present) occurring between the points in time of the ultrasound imaging with reference to the differential image.

In a version of the invention, marking means for marking, in the display of the ultrasound image, a region to be heated are provided, whereby the evaluation unit determines whether the location of an identified temperature change lies within the region intended to be heated. The location of a temperature change can thus be directly identified in the ultrasound image. In particular, it can be unambiguously found whether the heating in fact ensued within the region intended to be heated. Further marking means can be provided for marking a region in the ultrasound image which is to be examined that at least partially contains a region intended to be heated (which may itself be marked as above). The evaluation means then only determined temperature changes within the region to be examined. The outlay that must be incurred for identifying the temperature change and the location of the temperature can be clearly reduced in this way since only a limited region must be taken into consideration.

An installation for treating a living subject with radiation that heats at least an internal region of the body of the subject is achieved in an installation according to the invention which includes a radiation source and an apparatus of the type set forth above whose ultrasound imaging system at least partially images the region to be heated within the body of the subject, which is then charged with radiation, and whose evaluation means identifies temperature-related data from the chronologically successive ultrasound images that are respectively allocated to the points in time of the ultrasound imaging. It is thus possible to undertake locating of the region to be heated with the ultrasound imaging system in a known way at the same time as the identification of the temperature-related data with respect to the region to be examined, since the region to be examined and the region to be heated at least partially coincide.

In a preferred embodiment, an ultrasound source that generates ultrasound waves converging at a focus is provided as the radiation source. The ultrasound imaging system, among other things, also images the focus of the ultrasound waves.

For the reasons already set forth, the evaluation unit preferably determines the temperature-related data in the form of temperature changes that ensued between points in time of the production of the corresponding ultrasound images.

In other embodiments of the invention, an output signal of the evaluation unit representing the temperature-related data is supplied to a control unit that, when a preselectable temperature change upwardly transgressed, suppresses the generation of the radiation or regulates the radiated power output of the radiation source. The regulation is such that a temperature increase by a pre-selectable temperature amount first ensues, no temperature change subsequently ensues via a pre-selectable time span, and the generation of the radiation is suppressed at the end of the pre-selectable time span. The safety of the subject to be treated is guaranteed in this way, since undesired or undesirably long-lasting heating is precluded.

In a further embodiment of the invention means for marking a region to be treated are provided, this region lying at least partially within the region to be examined, and an output signal of the evaluation unit representing the temperature-related data is supplied to a control unit. The control unit compares the data for that part of the region to be examined that lies outside the region to be treated to a threshold and, given upper transgression of the threshold, suppresses the output of heating radiation. Given a suitable selection of the threshold, it is assured in this way that heating outside the region to be treated can be recognized so early that tissue damage is precluded. Tissue damage can be avoided with even greater reliability when the heating radiation output between two successive ultrasound images has an intensity that continuously rises proceeding from an initial value to a final value, since heating occurring outside the region to be treated can thus already be recognized so early that the intensity of the heating radiation is not yet adequate in order to produce tissue damage.

In a further embodiment of the invention means for marking a region to be treated are provided, this region lying at least partially within the region to be examined, and an output signal of the evaluation unit representing the temperature-related data is again supplied to a control unit. In this embodiment, after the generation of a first ultrasound image, the control unit drives the radiation source for generating an output of radiation with such a diminished intensity that a detectable temperature change occurs but a therapeutic effect does not yet occur. After the production of a second ultrasound image, the control unit checks, with reference to the temperature-related data, whether the temperature difference that is acquired lies within or outside the region to be treated. The control unit then drives the radiation source for generating an output of radiation with an intensity adequate for a therapeutic effect when the acquired temperature change was acquired within the region to be treated. Tissue damage outside the region to be treated is practically precluded in this way, since a previous was made, with a signal whose intensity is harmless, as to whether the heating ensued or will ensue within the region to be treated.

DESCRIPTION OF THE PREFERRED EMBODIMENTS

Figure 1:
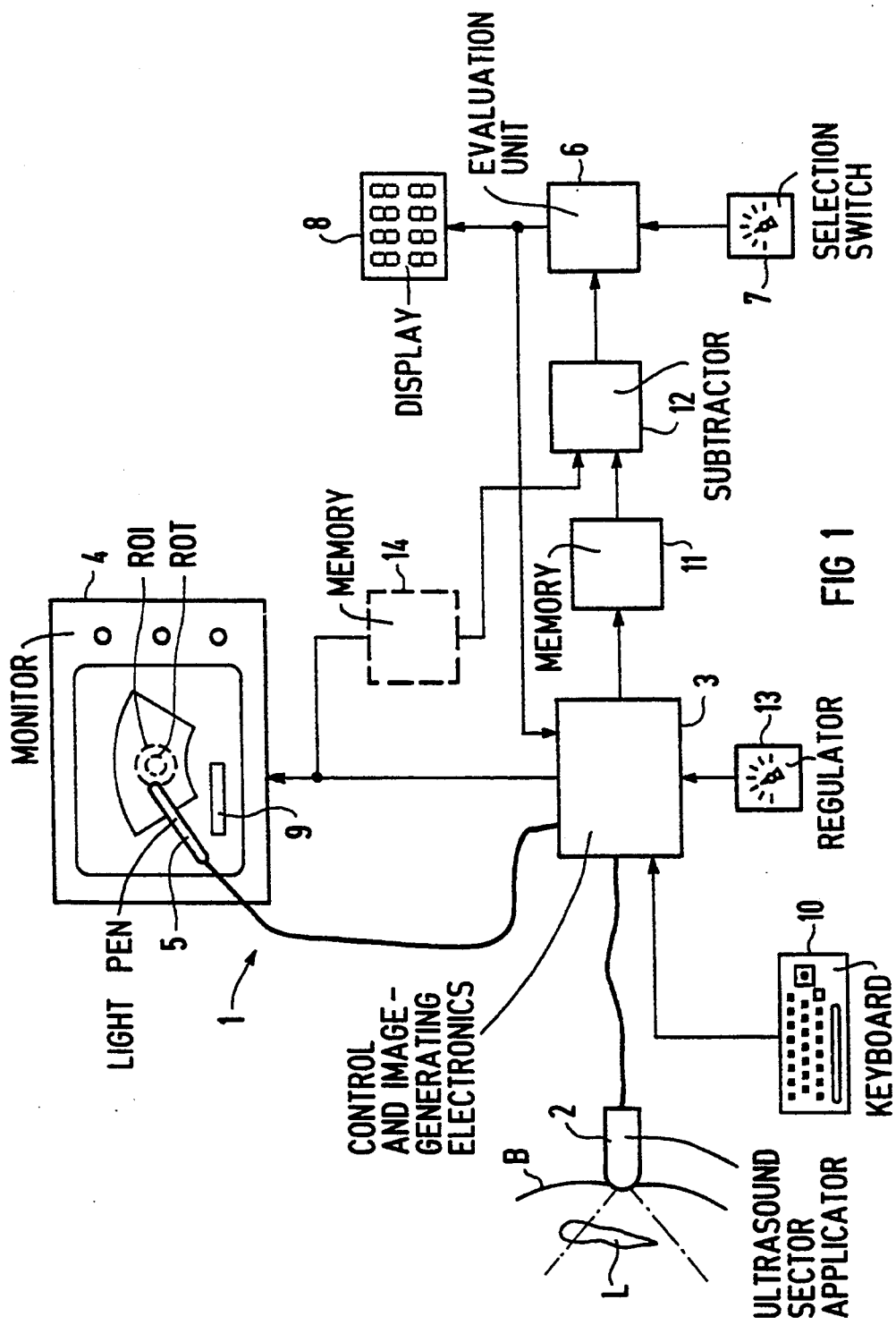
FIG. 1 shows an apparatus constructed in accordance with the principles of the present invention for temperature measurement, in the form of a block circuit diagram.

The apparatus of FIG. 1 includes an ultrasound imaging system generally referenced 1 which in terms of structure, corresponds to a conventional ultrasound B-imaging apparatus, or can be modified, commercially available apparatus of this type. The ultrasound imaging system 1 consequently includes an ultrasound sector applicator 2 connected to control and image-generating electronics 3, which interacts in a conventional way with the ultrasound sector applicator 2 to produce ultrasound B-sector images that are displayed on a monitor 4, which is likewise a component part of the ultrasound imaging system 1.

Marking means, such as a light pen 5, are also connected to the control and image-generating electronics 3, permitting marking of a region of interest ROI on the picture screen of the monitor 4. The image-generating electronics 3 effects the mixing into the ultrasound image of a mark ROI which corresponds to the contour marked with the light pen 5.

Data or signals corresponding to the generated ultrasound image, including the mixed-in mark, are supplied to an image memory 11, whose output is connected to an input of a subtractor 12. The subtractor 12 forms a differential image from an ultrasound image stored in the image memory 11 and a chronologically following ultrasound image. The corresponding output signal of the subtractor 12 is supplied to evaluation unit 6, which can be a separate electronic calculating unit or an image computer contained in the ultrasound imaging system 1 that is reprogrammed or modified from the commercially available program in a suitable way. The evaluation unit 6 determines temperature-related data on the basis of the changes in the acoustic impedance of the region of interest ROI that are caused if and when temperature change occurs between the points in time of the ultrasound imaging. These temperature-related data are in relationship to the temperature change that occurred between the points in time of the ultrasound imaging. The evaluation unit 6 supplies corresponding output signals to a display 8 that displays these data.

The ultrasound images, as is known, are produced by determining the impedance for different regions of the examination subject that are scanned with the ultrasound sector applicator and different acoustic impedances are displayed in different gray-scale or chromatic values. Therefore, changes in the acoustic impedance that are caused by temperature changes can be easily acquired in the described way in accordance with the invention. The formation of differential images is especially advantageous, since even slight changes of the acoustic impedance, and thus small changes in temperature, can be clearly recognized.

In order to be able to vary the length of the time span between the points in time of generating the ultrasound images that are supplied to the subtractor 12, a regulator 13 connected to the control and image-generating electronics 3 is provided. The length of this time span typically lies between 50 and 500 ms. Insofar as a limited image field is employed in comparison to conventional diagnostic ultrasound imaging, this time span may have a length on the order of magnitude of 10 ms.

In the embodiment of FIG. 1, a sector-shaped region of the body B of a subject under examination (indicated with broken lines in FIG. 1) is scanned with the ultrasound sector applicator such that an organ of interest, for example the liver L, is displayed in the ultrasound image, and the mark ROI is placed such that it lies in the ultrasound image within the region of the image of the liver L under examination. In this case, the evaluation unit 6 identifies temperature changes within the marked region of the liver L. The corresponding data, moreover, are supplied not only to the display 8, but also to the control and image-generating electronics 3, which mixes them into the ultrasound image in a field 9.

A selection switch 7 is connected to the evaluation unit 6, for selecting different media to be examined. Data correlating the dependency of the acoustic impedance on the temperature are stored for these different media in the evaluation unit 6, which permits changes in the acoustic impedance to be allocated to temperature changes in the described way. When the installation of FIG. 1 is employed exclusively for medical purposes, data for different tissue types, for example liver tissue, kidney tissue, etc., are stored. In case of non-medical application, data for other media, for example steel, aluminum, etc., are stored.

As a rule, moreover, the operation of the installation of FIG. 1 will ensue such that real-time ultrasound images are produced first, with the ultrasound sector applicator positioned relative to the subject under examination such that the region of interest is portrayed in the ultrasound images. The ultrasound image is then "frozen in", i.e. is stored in the image memory 11 and the stored image is continuously read out from the image memory 11 and displayed on the monitor 4. Subsequently, the mark ROI is made in the way already set forth with the light pen 5. The corresponding data are stored in the image memory 11. After the mark has been made, successive ultrasound images are generated, separated from one another by the time span set with the regulator 13. The evaluation unit 6 then identifies from the images the temperature change of the region lying within the mark ROI that occurs between successive ultrasound images in the way already set forth. If the evaluation unit 6 is operable with adequate speed, there is also the possibility of identifying and displaying the temperature change of the region under examination in real time.

The operation of the installation ensues via a keyboard-like operating part 10 connected to the control and image-generating electronics 3.

In general, the subtractor 12 subtracts the ultrasound image stored in the image memory 11 from the current ultrasound image obtained after the expiration of the chronological duration set with the regulator 13. In certain instances, for example when the chronological duration between two successive ultrasound images generated with the ultrasound imaging means I is shorter than the chronological data that the subtractor 12 requires for processing the data (or signals corresponding to the current ultrasound image), it can be expedient to also provide an image memory for the chronologically following image. Such an image memory 14 is indicated with dashed lines in FIG. 2. The installation then operates such that an ultrasound image is first stored in the image memory 11 and the current ultrasound image is then stored in the image memory 14 after the expiration of the chronological duration set with the regulator 13.

The installation of Figure I can be operated such that the temperature change is identified and displayed in response to a corresponding actuation of the keyboard 10, and this procedure is repeated only given a renewed actuation of the keyboard 10. It is possible to operate the installation of FIG. 1 in response to a corresponding actuation of the keyboard 10 such that the procedure of identifying the temperature change is automatically and continuously repeated. A new ultrasound image is then stored (overwritten) in the image memory 11 as soon as the data (or signals) corresponding to the proceeding, stored ultrasound image are no longer required. The formation of the difference from the corresponding, chronologically following ultrasound image is undertaken after the expiration of the chronological duration set with the regulator 13.

In another mode, it is possible in response to a corresponding actuation of the keyboard 10 to additionally mark a region of treatment ROT with the light pen 5, which lies at least partially within the region of interest ROI. The corresponding data are likewise stored in the ultrasound imaging system 1. When a temperature change is then detected during operation of the installation, the evaluation unit 6 determines the location of the temperature change with reference to the corresponding differential image. Additionally, the evaluation unit 6 determines whether the location of the temperature change lies within the region ROT intended to be heated or within that part of the region ROT intended to be heated that is located within the region of interest ROI. Corresponding data are mixed into the field 9, and an acoustic or optical alarm signal can be additionally generated when the temperature change lies outside the region of treatment ROT, or that part thereof situated inside the region of interest ROI. In response to a corresponding actuation of the keyboard 10, that region wherein the maximum of an identified temperature increase lies can be optionally displayed with increased brightness in the ultrasound image shown on the monitor 4. The described operation is particularly of significance when the installation of FIG. 1 is employed in conjunction with a therapy wherein a region located in the interior of the body of a patient is to be designationally heated, such as, for example, in hyperthermia or in thermotherapy.

Figure 2:
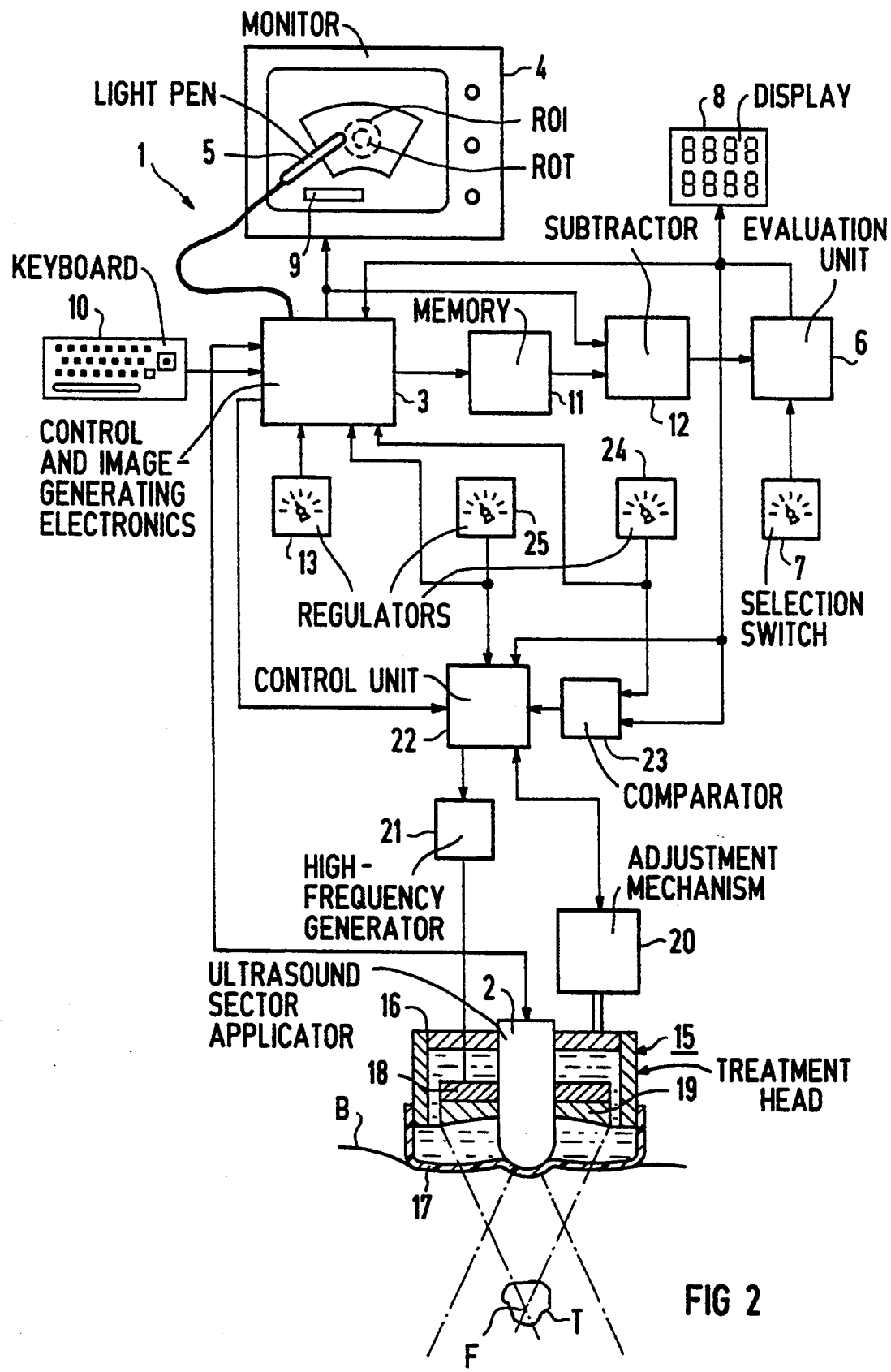
FIG. 2 shows an installation for treating a living subject with heating radiation constructed in accordance with the principles of the present invention.

FIG. 2 shows an apparatus for treating a living subject with radiation that heats at least an internal region of the body B of the subject and which contains a temperature-measuring apparatus largely corresponding to the apparatus of FIG. 1. For the implementation of a hyperthermia or thermotherapy regimen, a tumor T situated in the body B of the subject is to be heated, namely with focused ultrasound waves that are introduced into the body B with a treatment head generally referenced 15.

The treatment head 15 includes a tubular housing 16 having a closed base at one end and having an opposite end closed liquid-tight with a flexible application membrane 17. The housing 16 contains a fluid as the acoustic propagation medium for the ultrasound. The ultrasound energy is generated with, for example, a piezoelectric, planar ultrasound transducer 18 attached in the housing 16, which is preceded by an acoustic lens 19 for focusing the generated ultrasound onto a focus F. Instead of the planar piezoelectric ultrasound transducer 18 together with acoustic lens 19, focusing ultrasound transducers that deviate from the illustrated manner of focusing and ultrasound generating can be employed. The treatment head 15 has a central bore that extends through the base of the housing 16, through the ultrasound transducer 18 and through the acoustic lens 19. The ultrasound sector applicator 2 of the temperature-measuring means is accepted in this bore.

For the implementation of a treatment, the application membrane 17 of the treatment head 15, as shown in FIG. 2, is pressed against the body surface of the subject. The ultrasound sector applicator 2 presses against the body surface with the application membrane 17 therebetween in order to achieve good acoustic coupling. For implementing the treatment, the treatment head 15 must be aligned relative to the body B of the subject such that the focus F of the ultrasound, as shown in FIG. 2, comes to lie within the tumor T. This ensues with a known, preferably motorized adjustment mechanism 20 that is controlled as described below. A high-frequency generator 21 is provided for driving the ultrasound transducer 18 with an alternating voltage having the required frequency, amplitude and waveform.

The interaction of the treatment head 15 with the temperature-measuring device is defined by a control unit 22, the evaluation unit 6 and, if needed, a comparator 23. The control unit 22 controls the high-voltage generator 21 and is fashioned such that it is capable of activating or deactivating the latter, and also controls setting of the amplitude of the generated alternating voltage, and thus the intensity of the ultrasound waves that are produced. What intensity of the ultrasound waves is set is dependent on the state of a regulator 24 with which the desired temperature change of the zone of treatment, i.e. of the tumor T, can be selected. A signal corresponding to this temperature or temperature change is supplied to an input of the comparator 23. The corresponding output signal of the temperature-measuring apparatus is supplied to the other input of the comparator 23. As long as the output signal of the comparator 23 indicates that the temperature change selected with the regulator 24 has not yet been reached, ultrasound having an intensity selectable with the keyboard 10 is continuously generated with the ultrasound transducer 18. As soon as the temperature change selected with the regulator 24 has been reached, the control unit 22, taking the output signal of the comparator 23 into consideration, regulates the acoustic power of the ultrasound generated with the ultrasound transducer 18 such that (ignoring certain fluctuations caused by the regulation event) no further temperature change occurs for a selected time span, which that can be set with the regulator 25. The shortest time span that can be set with the regulator 25 is a time span of zero, i.e., the output of ultrasound is interrupted immediately after the occurrence of the preselected temperature change.

It is important to recognize in this context that, if the intensity of the ultrasound is so high that the tissue properties of the tumor irreversibly change, an unambiguous temperature dependency of the acoustic impedance may no longer be established under certain circumstances. Under these circumstances, only a qualitative identification of temperature changes that have occurred is still possible.

This, however, is less serious, particularly in the case of a therapy installation of the present type, since it is of far greater concern to know where a temperature change occurred then to know the exact size of the temperature change.

In the apparatus of FIG. 2, there is therefore the possibility in a further mode, as already set forth in conjunction with FIG. 1, to mark a region of treatment ROT. Given the occurrence of a temperature change, the evaluation unit 6 then identifies whether this occurred within the region of treatment ROT and an appropriate signal is supplied to the control unit 22. The data corresponding to the identified temperature increase are supplied to the comparator 23 which compares these data to a threshold set with the regulator 24, below which threshold no injury to healthy tissue is expected. When the identified temperature increase is limited to the region of treatment or the part thereof situated within the region of interest ROI, the control unit 22 then drives the ultrasound transducer 18 via the high-frequency generator 21 for a chronological duration selected with the regulator 25. If a temperature increase within the region of interest ROI also occurs outside the region of treatment ROT, the control unit 22 suppresses the output of ultrasound if and when the threshold of the temperature increase set with the regulator 24 is upwardly exceeded. The installation can then only be placed back into operation after a corresponding actuation of the keyboard 10.

In the described mode, the drive of the ultrasound transducer 18 preferably ensues such that the intensity of the ultrasound emitted by the ultrasound transducer 18 is continuously increased between two successive ultrasound images proceeding from an initial value, that is sure to be incapable of causing tissue damage, to a final value at which the desired therapeutic effect occurs. It is assured in this way that no tissue damage whatsoever can occur in the time span which elapses until the ultrasound emission is suppressed, since, given a suitable selection of the threshold set with the regulator 24, the emitted ultrasound does not yet have an intensity that could lead to damage in the event of an upward transgression of the threshold.

In a further mode, which likewise makes it necessary to mark the region of treatment ROT in the described way, the ultrasound transducer—after producing a first ultrasound image—is driven by the control unit 22 via the high-frequency generator 21 to emit ultrasound having such a reduced intensity that a temperature increase, detectable with the temperature-measuring apparatus, occurs but a therapeutic effect does not yet occur. After producing a second ultrasound image, the control unit 22 checks with reference to the signal supplied to it by the evaluation unit 6, whether the detected temperature increase lies inside or outside the region of treatment ROT. If the increase is inside the region ROT, the control unit 22 drives the ultrasound transducer 18 to emit ultrasound having an intensity that is adequate for a therapeutic effect. Following the production of the subsequent ultrasound image, ultrasound having a reduced intensity is again emitted in order to check whether the temperature increase produced as a result of the therapy emission lies within the region of treatment ROT. If so, ultrasound having an intensity adequate for a therapeutic effect is again emitted, and this sequence is repeated as many times as needed. If at any time the temperature increase produced by the ultrasound having reduced intensity lies outside the region of treatment ROT, the control unit 22 suppresses the emission of ultrasound having an intensity adequate for a therapeutic effect.

It is assured in these two latter modes that no therapeutic effect whatsoever occurs outside the region of treatment ROT. This is of special significance when the intensity of the ultrasound emitted for achieving a therapeutic effect is so high that the tissue lying in the focus of the ultrasound is necrotized.

The regulators 24 and 25, moreover, are also connected to the control and image-generating electronics 3. The control and image-generating electronics 3 mixes data corresponding to the settings of the regulators 24 and 25 into the field 9.

The ultrasound imaging system 1, the control unit 22 and the adjustment mechanism 20 cooperate such that, when a specific point of the ultrasound image displayed on the picture screen of the monitor 4 is tapped with the light pen 5 after an appropriate actuation of the keyboard 10, the control unit 22 actuates the adjustment mechanism 20 on the basis of data supplied from the control and image-generating electronics 3 such that the focus F of the ultrasound transducer 18 comes to lie in the point within the body B of the subject to be treated that corresponds to the point marked with the light pen 5. Insofar as a region of a treatment ROT is marked, the focus F is preferably constrained to be brought only into points that lie within the region of treatment ROT. The data or signals with respect to the current position of the treatment head 15 that are required for this automatic setting event are made available to the control unit 22 by the adjustment mechanism 20, which contains appropriate position sensors (not shown).

The treatment of a living subject with the described installation ensues in the following way:

The subject is first placed on a suitable bed support or the like such that that region of the body surface of the subject to which the treatment head 15 is to be applied is freely accessible. If necessary, the subject is restrained, so that the physical position of the subject can not significantly change. The treatment head 15 is then applied and, with the ultrasound imaging system 1 activated, is displaced relative to the body B of the subject until the region of treatment, the tumor T in the case of FIG. 2, can be clearly seen in the ultrasound image. The region of interest ROI of the temperature measurement and possibly the region of treatment ROT, are then marked with the light pen 5. One of the above-described modes is also selected. Subsequently, the selection switch 7 and the regulators 13, 24 and 25 are set at appropriate positions for the respective treatment. That point of the tumor T in which the focus F of the ultrasound waves should be located, and which normally lies within the marked region of treatment ROT, is then tapped in the ultrasound image with the light pen 5, whereupon the adjustment mechanism 20 correspondingly positions the treatment head 15. Thereafter, the ultrasound transducer 18 is activated in a manner corresponding to the selected mode.

Since the focus F of the ultrasound transducer 18, i.e., that region wherein an ultrasound intensity effective for a therapeutic effect is present, is usually smaller than the tumor T, in order to avoid damage to the sound tissue surrounding the tumor T it will usually be necessary to shift the focus F of the ultrasound transducer 18 step-by-step so often and such that the entire tumor T, or a marked region of treatment ROT is charged with ultrasound in the way set forth above. This procedure can be manually controlled with the assistance of the light pen 5 and of the keyboard 10. An automatic control of this procedure can also be provided whereby the entire tumor, or the region of the tumor situated within the marked region of treatment ROT, is "scanned". It is self-evident that only one slice of the tumor T is thus treated and that a displacement of the therapy head 15 perpendicularly relative to the slice imaged with the ultrasound imaging means 1 must ensue thereafter, whereby the successive slices arising in this way are treated in the above-described manner until, finally, the entire volume of the tumor T has been covered by the treatment.

Insofar as the operation of the installation of FIG. 2 does not ensue via the selection switch 7, the regulators 13, 24, 25 and the light pen 5, its operation is undertaken via the keyboard 10.

The installation of FIG. 2 is suitable not only for the treatment of tumors but can be employed whenever it is a desired to heat tissue regions in a defined way. Further, the heating need not necessarily ensue with focused ultrasound, it is also possible to effect the heating with, for example, a microwave applicator.

A perquisite for a reliable functioning of the described apparatus, of course, is that no movement of the subject under examination, or at least of the region of interest occurs between successive ultrasound images, since otherwise differences between successive ultrasound images that occur due to the movement could be incorrectly interpreted as temperature changes. Monitoring of the heart action (ECG) and respiration can be utilized for position or processing corrections.

In the installations of both FIGS. 1 and 2, moreover, the entire ultrasound image is utilized as the region of interest ROI if a corresponding mark with the light pen 5 is not made.

Also in the installations of both FIGS. 1 and 2, a quantitative acquisition of temperature changes that have occurred can be foregone if such information is not required, and an identification of the location of the temperature changes can instead exclusively ensue.

Ultrasound B-images are produced in the exemplary embodiments that have been set forth. This offers the advantage that a temperature change can be allocated to the corresponding location without further difficulty. It is also possible to produce ultrasound A-images instead of ultrasound B-images. Waveforms that correspond to those radiated into the subject for producing ultrasound images can also be employed when temperature changes are measured or detected without ultrasound images being produced.

A second image memory that corresponds to the image memory 14 of FIG. 1, moreover, can also be provided in the case of the installation of FIG. 2 as necessary.

As noted earlier, the apparatus of Figure I can also be employed for non-medical purposes.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for non-invasive measurement of a temperature change occurring between two points in time in a region of interest inside a subject, said method comprising the steps of:
    emitting a first ultrasound wave form, containing at least one ultrasound pulse, into said subject at a first point in time, said first ultrasound waveform being incident on said region of interest and said region of interest reflecting a corresponding first set of echo signals;
    receiving said first set of echo signals and generating a first ultrasound image therefrom and storing said first ultrasound image;
    emitting a second ultrasound waveform, identical to said first ultrasound waveform, into said subject at a second point in time, said second ultrasound waveform being incident on said region of interest and said region of interest reflecting a corresponding second set of echo signals;
    receiving said second set of echo signals and generating a second ultrasound image therefrom;
    generating a differential ultrasound image from said first and second ultrasound images; and
    allocating a temperature change of in said region of interest to said comparison result identifying a temperature change occurring in said region of interest between said first and second points in time from said differential ultrasound image.

2. A method as claimed in claim 1 wherein the steps of generating said first and second ultrasound images are further defined by generating a first ultrasound tomogram and generating a second ultrasound tomogram.

3. A method for non-invasively localizing a temperature change occurring between two points in time in a region of treatment in the inside of a living subject, said subject having a region of interest at least partially containing said region of treatment, said method comprising the steps of:
    emitting a first ultrasound waveform, containing at least one ultrasound pulse, into said subject at a first point in time, said first ultrasound waveform being incident on said region of interest and said region of interest reflecting a corresponding first set of echo signals:

receiving said first set of echo signals and generating a first ultrasound image therefrom and storing said first ultrasound image;

emitting a second ultrasound waveform, identical to said first ultrasound waveform, into said subject at a second point in time, said second ultrasound waveform being incident at said region of interest and said region of interest reflecting a corresponding second set of echo signals;

receiving said second set of echo signals and generating a second ultrasound image therefrom;

generating a differential ultrasound image from said first and second ultrasound images;

identifying from said differential ultrasound image whether a temperature change in said region of interest has occurred; and if a temperature change has occurred in said region of interest, determining from said differential ultrasound image whether said temperature change is within said region of treatment.

4. A method as claimed in claim 3 wherein the steps of forming said first and second ultrasound images are further defined by forming a first ultrasound tomogram and forming a second ultrasound tomogram.

5. An apparatus for non-invasively measuring a temperature change occurring between two successive points in time in a subject, comprising:

means for generating and displaying a first ultrasound image of said subject at a first point in time and a second ultrasound image of said subject at a second point in time;

means for storing said first ultrasound image;

means for subtracting said second ultrasound image from said first ultrasound image to obtain a differential ultrasound image; and evaluation means for determining a temperature change occurring between said first and second points in time from said differential ultrasound image.

6. An apparatus as claimed in claim 5 further comprising marking means for marking a region of interest and for mixing a respective mark into at least said first or second ultrasound image, and wherein said evaluation means comprises means for determining said temperature change within said region of interest.

7. An apparatus as claimed in claim 5 further comprising further memory means for storing said second ultrasound image prior to subtracting said second ultrasound image from said first ultrasound image.

8. An apparatus as claimed in claim 5 wherein said means for generating and displaying said first and second ultrasound images comprises means for generating and displaying first and second ultrasound tomograms.

9. An apparatus as claimed in claim 8 wherein said means for generating and displaying first and second ultrasound tomograms comprises means for generating and displaying first and second ultrasound B-images.

10. An apparatus for non-invasively measuring a temperature change occurring between two successive points in time in a subject, comprising:

means for generating and displaying a first ultrasound image of said subject at a first point in time and a second ultrasound image of said subject at a second point in time;

means for storing said first ultrasound image;

means for subtracting said second ultrasound image from said first ultrasound image to obtain a differential ultrasound image; and evaluation means for determining the location of the temperature change occurring between said first and second points in time from said differential ultrasound image.

11. An apparatus as claimed in claim 10 further comprising marking means for marking a region of interest and for mixing a respective mark into at least said first or second ultrasound image, and wherein said evaluation means comprises means for determining the location of the temperature change within said region of interest.

12. An apparatus as claimed in claim 11 further comprising further marking means for marking a region of treatment within said region of interest, and wherein said evaluation means comprises means for determining whether the location of said temperature change lies within said region of treatment.

13. An apparatus as claimed in claim 10 further comprising marking means for marking a region of treatment and for mixing a respective mark into at least said first or second ultrasound image, and wherein said evaluation means comprises means for determining whether the location of said temperature change lies within said region of treatment.

14. An apparatus as claimed in claim 10 further comprising further memory means for storing said second ultrasound image prior to subtracting said second ultrasound image from said first ultrasound image.

15. An apparatus as claimed in claim 10 wherein said means for generating and displaying said first and second ultrasound images comprises means for generating and displaying first and second ultrasound tomograms.

16. An apparatus as claimed in claim 15 wherein said means for generating and displaying first and second ultrasound tomograms comprises means for generating and displaying first and second ultrasound B-images.

17. An installation for administering treatment to a living subject, said treatment elevating the temperature of at least an internal region of the body of said subject, said installation comprising:

a radiation source for temperature-elevating radiation;

means for generating and displaying a first ultrasound image of a region of interest of said subject at a first point in time, said region of interest at least partially containing a region of treatment at which said temperature-elevating radiation is to be directed, and for generating a second ultrasound image of said region of interest at a second point in time;

means for storing said first ultrasound image;

means for subtracting said second ultrasound image from said first ultrasound image to obtain a differential ultrasound image; and means for evaluating said differential ultrasound image for identifying temperature changes in said differential ultrasound image caused by said temperature-elevating radiation.

18. An installation as claimed in claim 17 wherein said temperature-elevating radiation source comprises means for generating ultrasound waves converging at a focus, and wherein said means for generating and displaying said first and second ultrasound images comprises means for generating and displaying said first and second ultrasound images with said focus, imaged in said first and second ultrasound images.

19. An installation as claimed in claim 17 wherein said evaluation means generates an output signal corresponding to said temperature change, and said apparatus further comprising:
comparator means for comparing said output signal of said evaluation means to a predetermined temperature change; and
means for suppressing generation of said temperature-elevating radiation from said source if said output signal of said evaluation means upwardly transgresses said predetermined temperature change.

20. An installation as claimed in claim 17 wherein said evaluation means generates an output signal corresponding to said temperature change, wherein said radiation source generates said temperature-elevating radiation at a radiated output power, and said installation further comprising means, supplied with said output signal of said evaluation means, for regulating said radiated output power of said temperature-elevating radiation source dependent on said output signal of said evaluation means for initially causing a predetermined temperature increase in said region of interest, causing no temperature change in said region of interest for a time span following attainment of said predetermined temperature increase, and for suppressing generation of said temperature-elevating radiation at an end of said predetermined time span.

21. An installation as claimed in claim 20 further comprising means for selecting a length of said time span.

22. An installation as claimed in claim 17 wherein said evaluation means generates an output signal corresponding to said temperature change, and said installation further comprising: means for marking a region of treatment and for mixing a respective mark into a least said first or second ultrasound image of said region of interest; and control means for comparing said output signal of said evaluation means corresponding to temperature changes in said region of interest which are outside of said region of treatment to a threshold and for suppressing generation of said temperature-elevating radiation upon upward transgression of said threshold by said output signal.

23. An installation as claimed in claim 22 wherein said radiation source generates said temperature-elevating radiation at an intensity, and wherein said installation further comprises means for regulating generation of said temperature-elevating radiation from said source between said first and second points in time by controlling said source to generate said radiation at an intensity which continuously rises from an initial value to a final value.

24. An installation as claimed in claim 17 wherein said evaluation means generates an output signal corresponding to said temperature change, and said installation further comprising:
means for marking said region of treatment and for mixing a respective mark into at least said first or second ultrasound image; and
control means, supplied with said output signal from said evaluation means, for controlling operation of said radiation source dependent on said output signal for driving said source, after generation of said first ultrasound image, to emit radiation having a first intensity sufficient to cause a temperature change detectable by said evaluation means but insufficient to have a therapeutic effect on said subject and, after generation of said second ultrasound image, for identifying whether said temperature difference is inside said region of treatment and, if said temperature difference is inside said region of treatment, for driving said source to emit radiation having an intensity sufficient for having a therapeutic effect on said subject.

* * * * *